(12) United States Patent
Bruns et al.

(10) Patent No.: US 8,563,768 B2
(45) Date of Patent: Oct. 22, 2013

(54) PROCESS FOR THE PREPARATION OF ISOCYANATES

(75) Inventors: Rainer Bruns, Leverkusen (DE); Wolfgang Lorenz, Dormagen (DE); Friedhelm Steffens, Leverkusen (DE); Herbert Stutz, Dormagen (DE)

(73) Assignee: Bayer MaterialScience AG, Leverkusen (DE)

( * ) Notice: Subject to any disclaimer, the term of this patent is extended or adjusted under 35 U.S.C. 154(b) by 85 days.

(21) Appl. No.: 13/382,615

(22) PCT Filed: Jun. 26, 2010

(86) PCT No.: PCT/EP2010/003916
§ 371 (c)(1),
(2), (4) Date: Feb. 1, 2012

(87) PCT Pub. No.: WO2011/003532
PCT Pub. Date: Jan. 13, 2011

(65) Prior Publication Data
US 2012/0123152 A1    May 17, 2012

(30) Foreign Application Priority Data
Jul. 9, 2009  (DE) .......................... 10 2009 032 413

(51) Int. Cl.
*C07C 263/10*   (2006.01)
(52) U.S. Cl.
USPC ........................................................ 560/347
(58) Field of Classification Search
USPC ........................................................ 560/347
See application file for complete search history.

(56) References Cited

U.S. PATENT DOCUMENTS

| 2,764,607 | A | | 9/1956 | Hieserman |
| 3,381,025 | A | * | 4/1968 | Mitsumori et al. ........... 560/347 |
| 4,847,408 | A | | 7/1989 | Frosch et al. |
| 5,449,818 | A | | 9/1995 | Biskup et al. |
| 7,584,629 | B2 | | 9/2009 | Sohn et al. |
| 7,915,444 | B2 | | 3/2011 | Woelfert et al. |
| 2010/0041915 | A1 | | 2/2010 | Woelfert et al. |
| 2010/0217035 | A1 | | 8/2010 | Knoesche et al. |

FOREIGN PATENT DOCUMENTS

| EP | 1849767 A1 | 10/2007 |
| GB | 737442 | 9/1955 |
| GB | 1165831 | 10/1969 |

* cited by examiner

*Primary Examiner* — Brian J Davis
(74) *Attorney, Agent, or Firm* — Robert S. Klemz; Lyndanne M. Whalen

(57) ABSTRACT

An isocyanate is produced by reacting an amine with a stoichiometric excess of phosgene in the gas phase. This reaction is carried out at a temperature above the amine's boiling point to obtain a liquid stream containing the isocyanate and a gas stream containing hydrogen chloride and phosgene. The gas stream containing hydrogen chloride and phosgene thus produced is separated into a gas stream containing hydrogen chloride and a liquid stream containing phosgene. At least part of the liquid stream containing phosgene is then converted to a gas stream containing phosgene which gas stream is then recycled. The gaseous phosgene stream is maintained at a higher pressure than the liquid phosgene stream.

8 Claims, No Drawings

PROCESS FOR THE PREPARATION OF ISOCYANATES

The invention relates to a process for the preparation of isocyanates by reacting primary amines with a stoichiometric excess of phosgene in the gas phase, wherein the excess phosgene is then recovered and recycled into the reaction.

Isocyanates are prepared in large quantities and are used mainly as starting materials for the preparation of polyurethanes. They are usually prepared by reacting the appropriate amines with phosgene, the latter being used in stoichiometric excess. The reaction of the amines with the phosgene can take place either in the gas phase or in the liquid phase. In these syntheses, at least part of the excess phosgene is normally obtained together with the gaseous hydrogen chloride by-product liberated in the reaction, so it is indispensable, for an economic operation of an isocyanate synthesis, to separate the excess phosgene from the hydrogen chloride by-product and recycle it into the reaction.

The present invention relates in particular to a process for recovery of the excess phosgene obtained in the preparation of isocyanates from amines and phosgene in gas-phase phosgenation, and for recycling of the recovered phosgene into the gas-phase reactor.

Various processes for the preparation of isocyanates by reacting amines with phosgene in the gas phase are known from the state of the art.

EP-A-289 840 describes the preparation of aliphatic diisocyanates by gas phase phosgenation, the phosgene being used in excess. The patent document describes that the excess phosgene can be removed in a manner known per se from the gas stream leaving the reaction, and mentions a cold trap or absorption in a solvent at a temperature of −10° C. to 8° C., or adsorption and hydrolysis on activated charcoal. In Example 1 the phosgene is removed from the gas stream leaving the reaction by adsorption in an activated charcoal tower. The document teaches that the flow rate in the reaction chamber can be adjusted by applying a differential pressure between the feed lines into the chamber and the exit out of the chamber, but does not disclose how the differential pressure is produced. A particular disadvantage of the disclosed process is that in a work-up of this kind the excess phosgene is destroyed and can no longer be used in the reaction, so the operation is not economic.

EP-A-570 799 relates to a process for the preparation of aromatic diisocyanates, characterized in that the reaction of the appropriate diamine with excess phosgene is carried out in a tubular reactor above the boiling point of the diamine for a mean contact time of 0.5 to 5 seconds. The patent document describes that the phosgene can be removed in a manner known per se from the gaseous mixture leaving the condensation stage of the reactor, and mentions a cold trap, absorption in a cold solvent and adsorption and hydrolysis on activated charcoal. The Example describes hydrolysis of the excess phosgene with water. This destruction of the excess phosgene is disadvantageous in terms of an economic procedure.

GB-A-1 165 831 describes a process for the preparation of isocyanates in the gas phase, wherein the reaction of the amine vapour with the phosgene is carried out at temperatures between 150° C. and 300° C. in a tubular reactor equipped with a mechanical stirrer and capable of being thermostatted by a heating jacket. One disadvantage of the disclosed process is the use of a high-speed stirrer and its external drive via a shaft passing through the reactor wall, because, when phosgene is used, the sealing of this type of stirrer that is necessary to comply with safety regulations is very expensive. The Example describes that the vapours leaving the reactor are absorbed in cold monochlorobenzene. No instructions are given regarding whether and in what way the phosgene absorbed in the solvent can be re-used in the reaction.

GB 737 442 describes a process for the recovery of liquid phosgene from gaseous mixtures containing HCl and phosgene, characterized in that the gaseous mixture flows upwards through a condenser cooled to −40 to −60° C., the phosgene condensing and running off into a storage tank. This patent document does not disclose how the recovered liquid phosgene can be used in a gas-phase reaction. One disadvantage of the disclosed process is that the HCl gas leaving the condenser still contains significant amounts of phosgene, which are thus lost for the phosgenation reaction. Another disadvantage is that the temperature level at which the condensation is carried out is very low and hence costly in energy terms.

U.S. Pat. No. 2,764,607 describes a process for the recovery of phosgene from a gaseous mixture with HCl originating from the production of chloroformates. For this purpose the gas which has left the condenser fitted to the reaction vessel is first brought into contact with cold solvent, the phosgene being absorbed in said solvent. This is followed by an extraction step in which the phosgene, together with the partially co-absorbed HCl, is continuously separated from the solvent in a distillation column. This is followed in turn by purification of the resulting gas stream by condensation of the solvent, and then by liquefaction of the phosgene, which is led into a liquid storage container. The patent document discloses no teaching as to what pressure ratios prevail between the absorption step and the extraction step. A disadvantage of the disclosed process is that the storage of liquid phosgene carries a high potential risk.

According to the teaching of EP 1 849 767, an economic isocyanate production process requires separating and recovering the excess phosgene from the HCl coupling product and obtaining the HCl in sufficient purity for it to be usable in other syntheses and fields of application without further treatment. For this purpose the patent document discloses a process in which the gaseous mixture is absorbed in a solvent in two stages, the first step being carried out isothermally and the second adiabatically. This yields a solution of phosgene in the absorption medium and an HCl gas of the desired purity. The document describes that, for isocyanate productions by the gas-phase process, the phosgene solution obtained can be desorbed in a subsequent step. According to the teaching of EP 1 849 767, the absorption is preferably carried out at low temperatures and high pressures and the desorption is preferably carried out at high temperatures and low pressures.

DE 102 600 84 describes an alternative process for the separation of gaseous mixtures made up of hydrogen chloride and phosgene. The patent document discloses a process wherein the phosgene is condensed under elevated pressure and the condensed phase is stripped in a subsequent process step in order to remove the hydrogen chloride from the phosgene bottom product, i.e. in the liquid phase. The stripping is necessary because significant amounts of HCl dissolve in the condensate on account of the elevated pressure and, according to the document's teaching, have a disadvantageous effect in phosgenation reactions. A disadvantage of the disclosed process is that, because of the prevailing condensation pressure, a further process step is necessary in order to separate off the dissolved HCl. The document provides no instructions regarding the recovery of gaseous phosgene. It describes that the HCl/phosgene separation can be carried out under high pressure, although this increases the safety risk. Moreover, the production of high pressure is costly in energy terms. Very low temperature separation is described as an alternative, but again this has a high energy cost and also leads to high contents of HCl in the liquid phase containing phosgene.

WO 2007 014 936 discloses a process for the preparation of diisocyanates by reacting diamines with a stoichiometric excess of phosgene, wherein at least part of the excess phosgene is recycled into the reaction and wherein the phosgene stream entering the reactor prior to mixing with the amine contains less than 15 wt. % of HCl. Said patent document teaches that this is supposed to improve the working life of the reactors by reducing precipitations of amine hydrochlorides. A disadvantage of such high contents of inert HCl gas in the phosgene gas is that this entails large apparatuses and hence high plant construction costs. Furthermore, the inert HCl gas in the phosgene gas increases the circulating streams, resulting in increased operating costs. Thus it is generally always desirable to minimize the inert gas burden on the processes. An embodiment is described in which firstly the excess phosgene and the hydrogen chloride formed are separated from the essentially gaseous reaction mixture, and then at least part of the excess phosgene is recycled into the reaction, hydrogen chloride being separated from this recycled phosgene in such a way that the phosgene stream prior to mixing with the amine stream contains less than 15 wt. % of HCl. The document describes that the separation is preferably carried out by means of a combination of distillation and washing: a detergent is used to wash the phosgene out of the stream containing hydrogen chloride, and the phosgene and hydrogen chloride are preferably separated from this loaded washing medium by distillation. According to the description, the washing and distillation can be operated at pressures of 1 to 10 bar absolute. The document does not disclose the relative pressure ratios between the washing and the distillation.

According to the teaching of WO 2008 086 922, in a gas-phase phosgenation reaction, the phosgene prior to mixing with the amine must not contain more than 1000 ppm by weight of chlorine, since otherwise there would be a risk of material embrittlement due to the high temperatures. According to this teaching, a certain amount of chlorine always forms due to the decomposition of phosgene at high temperatures, so it is necessary to separate this chlorine off. For this purpose the patent document discloses a procedure in which firstly the gaseous mixture containing phosgene, HCl and chlorine is subjected to partial condensation (p. 18, l. 30) and washing (p. 19, l. 18), in each case at a pressure of 0.1 to 20 bar absolute. This produces a liquid phase containing phosgene, washing medium, HCl and chlorine, from which the low boilers—chlorine and HCl—are then removed by rectification at a pressure of 1 to 5 bar absolute. In a subsequent step the phosgene and washing medium are separated from each other by rectification at a pressure of 1 to 5 bar absolute (p. 21, l. 2), giving a phosgene stream of the desired chlorine purity which can be re-used in the phosgenation. According to the general teaching of this document, it is thus advantageous to operate the partial condensation and washing under a higher pressure than the rectification steps. Furthermore, according to the teaching of this document, a two-stage distillation process is needed to obtain gaseous phosgene of adequate purity for a phosgenation reaction from a washing medium loaded with phosgene.

WO 2009 037 179 discloses a process for the preparation of isocyanates in the gas phase, wherein the phosgene is in essentially gaseous form in all the process steps, so it is no longer necessary to supply energy to evaporate liquid phosgene. According to the teaching of the patent document, this is achieved by a process in which the gaseous phosgene obtained in the phosgene production is introduced into the gas-phase phosgenation especially without intermediate condensation.

Said document further describes a process for the separation of phosgene from a gaseous mixture with HCl and recycling of the separated phosgene into the gas-phase phosgenation by means of a combination of washing and multistage distillation operated under a pressure of 1 to 10 bar absolute. The document does not disclose the relative pressure ratios between the washing and the distillation.

The document explains that, in a first step, washing of the gaseous phosgene/HCl mixture with a washing liquor produces a washing liquor loaded with phosgene and HCl. This is followed by a first distillation step in which the HCl is removed as far as possible from the phosgene-containing washing solution and recycled into the upstream washing step. There then follows a second distillation step in which the previously obtained washing solution is separated into gaseous phosgene and washing liquor containing as little phosgene as possible. The gaseous phosgene is directed into the gas-phase phosgenation, while the washing liquor is re-used for washing the gaseous phosgene/HCl mixture. According to the general teaching of this document, a two-stage distillation process with recycling of the HCl into the upstream wash is therefore needed to recover phosgene from gaseous mixtures containing phosgene and HCl, and to be able to use it for a gas-phase phosgenation.

Surprisingly, it has now been found that a sequence of two process steps is particularly suitable for the recovery of phosgene from gaseous mixtures containing phosgene and HCl, such as those formed by reacting a stoichiometric excess of phosgene with primary amines in a reactor, and for the subsequent recycling of the recovered phosgene into the reactor. In the first step of this process (HCl/phosgene separation) the gaseous mixture containing HCl and phosgene leaving the reactor is separated into a gas stream containing essentially HCl and a liquid stream containing phosgene, and in a second step (phosgene gas production) at least part of the previously obtained liquid stream is converted to a gas stream containing phosgene, the pressure in the first process step being lower than the pressure in the second process step. Using the process according to the invention with the process conditions according to the invention makes it possible to dispense with pressure-raising elements in the gas path of the phosgene recycled into the reactor. This increases the safety of the production plant. In particular, it enables pressure-raising elements to be dispensed with in the whole of the phosgene gas space, and the process according to the invention makes it possible to recover gaseous phosgene from gaseous mixtures containing phosgene and HCl without having to recycle a gas stream from the second process step of phosgene gas production into the first process step of HCl/phosgene separation. This reduces the number of apparatuses and lowers the energy costs of the process.

The process according to the invention, in combination with the required process conditions, affords a high phosgene recovery yield, i.e. a high proportion of the phosgene is separated from the gaseous mixture containing phosgene and HCl, and recycled into the reaction. This minimizes the phosgene losses and improves the economy of the process.

Using the required process sequence in combination with the required operating conditions in the process according to the invention is particularly surprising insofar as, according to the teaching of the state of the art, the conversion of phosgene from the liquid phase to the gas phase is (in energy terms) advantageously operated at a lower pressure than the upstream separation of the phosgene from the gaseous HCl/ phosgene mixture, e.g. by absorption of the phosgene in an absorption medium and subsequent desorption.

In this respect, in view of the state of the art, those skilled in the art could not have expected that a procedure in which the pressures were reversed between the process steps of HCl/phosgene separation and phosgene gas production would lead to an advantageous overall process in energy terms.

Surprisingly, it has also been found that the first process step of HCl/phosgene separation, operated under a lower pressure than the phosgene gas production, produces an HCl gas that is sufficiently pure for further processing, despite the low pressure. This is surprising because, according to the teaching of the state of the art, the purity of the HCl gas produced in the first process step increases with the pressure prevailing in this step.

It is particularly surprising for those skilled in the art that, despite the low pressure in the first process step of HCl/phosgene separation, as much of the phosgene as possible can be separated from the gaseous mixture containing HCl and phosgene, whereby the phosgene losses are low in this process stage. Combined with the fact that it is no longer necessary to recycle gas from the second process step of phosgene gas production into the first process step of HCl/phosgene separation, this affords a high phosgene recovery yield.

Using the process sequence provided for in the process according to the invention is advantageous because the stream produced in the first step of HCl/phosgene separation only contains small amounts of dissolved HCl and dissolved inert gases. This is particularly advantageous because it reduces the inert gas burden on the apparatuses in the process steps of phosgene gas production and reaction, and hence enables these apparatuses to be built smaller. It is moreover also advantageous because the energy cost of producing the phosgene gas in the following process step is reduced due to the small amount of dissolved HCl. Furthermore, it is possible to omit the two-stage distillation (necessary according to the state of the art) with recycling of an HCl gas stream into the HCl/phosgene separation, so a gas stream does not have to be recycled from the second process step of phosgene gas production into the first process step of HCl/phosgene separation. By choosing the appropriate process parameters in the HCl/phosgene separation, the content of dissolved HCl and dissolved inert gases in the liquid stream produced in the first process step can be adjusted so that no adverse effect on the reaction can be detected.

A high phosgene recovery yield can be achieved by the process according to the invention in combination with the process conditions according to the invention.

Thus, using the process according to the invention with the required process conditions affords an energetically advantageous phosgene recovery and recycling of the phosgene into the phosgenation reaction, on the one hand, and increases the safety of the process, on the other. Also, the process according to the invention allows the phosgene recovery and phosgene recycling to be carried out with a smaller number of apparatuses, thereby enabling the investment costs to be reduced.

The invention relates to a process for the preparation of isocyanates by reacting primary amines with a stoichiometric excess of phosgene in the gas phase, wherein
  a) the amine is reacted with phosgene in a reactor above the boiling point of the amine to give a liquid stream containing the isocyanate and a gas stream containing HCl and phosgene,
  b) the gas stream containing HCl and phosgene obtained in step a) is first separated into a gas stream containing HCl and a liquid stream containing phosgene,
  c) at least part of the liquid stream containing phosgene obtained in step b) is then converted to a gas stream containing phosgene, and
  d) the gas stream containing phosgene obtained in step c) is recycled into the reaction in step a),
  e) the pressure of the gas stream containing phosgene obtained in step c) being higher than the pressure of the liquid stream containing phosgene obtained in step b).

Gas-Phase Phosgenation (Step a))

The phosgenation of amines in the gas phase by reaction with phosgene in step a) is generally known from the state of the art (e.g. EP-A-570 799, WO-A-2007/014936).

It is preferable here to use primary amines. Preference is afforded to primary aromatic amines, especially primary aromatic diamines, which can be converted to the gas phase essentially without decomposition.

Examples of preferred aromatic amines are toluylenediamine (TDA), especially 2,4-TDA and 2,6-TDA and mixtures thereof, diaminobenzene, naphthyldiamine (NDA) and 2,2'-, 2,4'- or 4,4'-methylenediphenyldiamine (MDA) or isomer mixtures thereof. Particular preference is afforded to toluylenediamine (TDA), especially 2,4-TDA and 2,6-TDA and mixtures thereof.

Other suitable examples are particularly amines, especially diamines, that are based on aliphatic or cycloaliphatic hydrocarbons having 2 to 18 carbon atoms. Particularly suitable amines are 1,6-diaminohexane, 1-amino-3,3,5-trimethyl-5-aminomethylcyclohexane (IPDA) and 4,4'-diaminodicyclohexylamine.

Before the process according to the invention is carried out, the starting amines are normally evaporated and heated to 200° C. to 600° C., preferably to 200° C. to 500° C. and particularly preferably to 250° C. to 450° C., and fed into the reaction chamber optionally diluted with an inert gas such as $N_2$, He or Ar, or with the vapours of an inert solvent, e.g. optionally halogen-substituted aromatic hydrocarbons such as chlorobenzene or o-dichlorobenzene.

The starting amines can be evaporated in any of the known evaporation apparatuses. Preference is afforded to evaporation systems in which a small operating hold-up is passed with a high circulation capacity through a falling-film evaporator, where, to minimize the thermal stress on the starting amines, the evaporation process—as mentioned above—can optionally be supported by introducing inert gas and/or vapours of an inert solvent. Alternatively, the evaporation can also take place in special evaporation apparatuses with very short residence times, as described e.g. in EP 1 754 698.

In the process according to the invention, it is advantageous to use the phosgene in excess relative to the amine groups to be reacted. The molar ratio of phosgene to amine groups is preferably 1.1:1 to 20:1, particularly preferably 1.2:1 to 5:1. The phosgene is also heated to temperatures of 200° C. to 600° C. and fed into the reaction chamber optionally diluted with an inert gas such as $N_2$, He or Ar, or with the vapours of an inert solvent, e.g. optionally halogen-substituted aromatic hydrocarbons such as chlorobenzene or o-dichlorobenzene.

The process according to the invention is carried out in such a way that the separately heated reactants are introduced into at least one reaction chamber via at least one mixing device, mixed, and reacted, preferably adiabatically, while observing appropriate reaction times. The isocyanate is then condensed by cooling the gas stream down to a temperature above the decomposition point of the corresponding carbamic acid chloride, e.g. the acid chloride of toluylenediamine in the case of TDA.

The residence time required to react the amine groups with the phosgene to form isocyanate is between 0.05 and 15 seconds, depending on the type of amine used, the starting temperature, the adiabatic temperature rise in the reaction chamber, the molar ratio of amine used to phosgene, any dilution of the reactants with inert gases, and the chosen reaction pressure.

If, for the system in question (amine used, starting temperature, adiabatic temperature rise, molar ratio of reactants, diluent gas, reaction pressure), a previously determined minimum residence time for completion of the reaction is exceeded by less than 20%, preferably by less than 10%, the formation of secondary reaction products, such as isocyanurates and carbodiimides, can be extensively avoided.

Both the mixing of the reactants as homogeneously as possible, and the further reaction, have to take place within this spectrum of contact times, which is very narrow for chemical reactions. The further reaction preferably takes place without back-mixing as this would widen the contact period and hence increase the formation of unwanted by-products and secondary products.

When the process is carried out in practice, a deviation from the mean contact time can arise because of the time required to mix the reactants. The methods of implementing short mixing times are known in principle, suitable examples being mixing units or mixing chambers with mobile or static mixing components or nozzles. It is preferable to use static mixers in mixing chambers, as described e.g. in EP-A-1 362 847, EP-A-1 526 129 or EP-A-1 555 258. The process according to the invention preferably uses the apparatuses disclosed in paragraphs (0008) to (0014) and (0023) to (0026) of EP-A-1 362 847, paragraphs (0008) to (0013) and (0022) to (0026) of EP-A-1 526 129 or paragraphs (0007) and (0024) to (0025) of EP-A-1 555 258.

It is particularly preferable to use reactors with essentially rotationally symmetric reaction chambers where the gaseous educts, optionally diluted with inert gases, are fed into the at least one mixing chamber according to the jet mixer principle (Chemie-Ing. Techn. 44 (1972) p. 1055, FIG. 10). The material streams fed in enter the at least one mixing chamber of the reactors with a rate ratio preferably of 2-20, particularly preferably of 3-15 and very particularly preferably of 4-12. Preferably, the amine, optionally diluted with inert gases, is fed into the at least one mixing chamber of the reactors at the higher flow rate.

Preferably, neither the reaction chamber nor any mixing units or mixing chambers have heating surfaces, which can give rise to thermal stress resulting in secondary reactions such as isocyanurate or carbodiimide formation, or cooling surfaces, which can give rise to condensation resulting in sedimentation. Thus, apart from any radiation and dissipation losses, the components are preferably reacted adiabatically, the adiabatic temperature rise in the mixing unit and the reactor, or the reactor alone, being adjusted via the temperatures, compositions and relative proportions of the educt streams and the residence time in the mixing units and the reactors. It is also possible to react the components non-adiabatically in the process according to the invention.

After the phosgenation reaction has taken place in the reaction chamber, the gaseous reaction mixture, which preferably comprises at least one isocyanate, phosgene and hydrogen chloride, is freed of the isocyanate formed. This can be done e.g. by a procedure in which the mixture continuously leaving the reaction chamber, which preferably comprises at least one isocyanate, phosgene and hydrogen chloride, is condensed in an inert solvent after it has left the reaction chamber, in the manner already recommended for other gas-phase phosgenations (EP-A-0 749 958).

Preferably, however, the condensation is carried out as follows: The reaction chamber used in the process according to the invention has at least one zone into which one or more suitable liquid streams ("quenching liquors") are sprayed in order to stop the reaction between the amines used and the phosgene to form the corresponding isocyanates. As described in EP-A-1 403 248, this can cool the gaseous mixtures rapidly without using cold surfaces.

In one particularly preferred form of the process according to the invention, the at least one zone (cooling zone) is integrated with a quenching stage, as disclosed e.g. in EP-A-1 403 248. In one particularly preferred form, several cooling zones are used, these at least two cooling zones being integrated and operated with a quenching stage. This is disclosed in EP-A-1 935 875 in respect of design and operation.

As an alternative to the integrated coupling of the at least one cooling zone of a reactor with a quenching stage, as disclosed in EP-A-1 935 875, it is also possible to have the corresponding integrated coupling of the cooling zones of several reactors with a quenching stage. However, preference is afforded to the integrated coupling of the at least one cooling zone of a reactor with a quenching stage.

In one preferred embodiment of the process according to the invention, the throughput capacity of the reactor used with the reaction conditions required according to the invention is >1 t amine/h, preferably 2-50 t amine/h. These values apply particularly preferably to toluylenediamine, 1,6-diaminohexane and isophoronediamine. Throughput capacity is to be understood here as meaning that said throughput capacity of amine per h can be converted in the reactor.

Independently of the chosen type of cooling, the temperature of the at least one cooling zone is preferably chosen one the one hand so that it is above the decomposition point of the carbamoyl chloride corresponding to the isocyanate, and on the other hand so that the isocyanate and optionally the solvent concomitantly used as diluent in the amine vapour stream and/or phosgene stream condense as far as possible or dissolve in the solvent as far as possible, while excess phosgene, hydrogen chloride and inert gas optionally used concomitantly as diluent pass through the condensation or quenching stage as far as possible uncondensed or undissolved. Particularly suitable for obtaining the isocyanate selectively from the gaseous reaction mixture are solvents like chlorobenzene and/or dichlorobenzene kept at a temperature of 80 to 200° C., preferably at 80 to 180° C., or the isocyanate or mixtures of the isocyanate with chlorobenzene and/or dichlorobenzene kept in these temperature ranges. It is easy for those skilled in the art to predict, on the basis of the physical data for a given temperature, pressure and composition, what proportion by weight of isocyanate condenses in the quencher or passes through the quencher uncondensed. Likewise, it is easy to predict what proportion by weight of excess phosgene, hydrogen chloride and inert gas optionally used as diluent passes through the quencher uncondensed or dissolves in the quenching liquor.

The gaseous mixture leaving the condensation or quenching stage is preferably freed of residual isocyanate with a suitable washing liquor in a downstream gas scrubber.

Preferably, the isocyanates are then purified by distillative work-up of the solutions or mixtures from the condensation or quenching stage.

The gas stream containing at least HCl and phosgene obtained from step a) is then separated in step b) into a gas stream containing HCl and a liquid stream containing phosgene.

HCl/Phosgene Separation (Step b))

According to the invention, the gaseous mixture leaving step a), containing at least HCl and the unreacted excess phosgene from the reaction, is separated, in the HCl/phosgene separation in step b), into a gas stream containing essentially HCl and a liquid stream containing phosgene.

Together with the reaction coupling product, HCl, and the unreacted excess phosgene, the gaseous mixture coming from step a) and entering the separation in step b) can optionally also contain inert gases and/or solvents and/or reaction by-products and/or traces of the reaction product. Examples of inert gases which may be mentioned are nitrogen, helium, argon, excess CO from the phosgene production, and $CO_2$. Examples of reaction by-products which may be mentioned are the by-products of the phosgene production, such as carbon tetrachloride, chloroform, monochloromethane, $CO_2$ and methane.

The gaseous mixture entering the separation in step b) normally contains 1 to 50 wt. % of HCl, preferably 3-40 wt. % of HCl, particularly preferably 5-35 wt. % of HCl and very particularly preferably 7.5-30 wt. % of HCl, based on the weight of gaseous mixture. This gaseous mixture normally contains 5-90 wt. % of phosgene, preferably 15-85 wt. % of phosgene, particularly preferably 25-80 wt. % of phosgene and very particularly preferably 40-75 wt. % of phosgene, based on the weight of gaseous mixture. The solvent content of the gaseous mixture is normally 0.01-60 wt. %, preferably 0.05-40 wt. % and particularly preferably 0.1-10 wt. %, based on the weight of gaseous mixture. The solvent can be in either vapour or liquid form. The gaseous mixture can also contain inert gases normally totaling 0-10 wt. %, preferably 0.0001-8 wt. % and particularly preferably 0.001-5 wt. %, based on the weight of gaseous mixture. The gaseous mixture can normally contain 0-10 wt. %, preferably 0.001-7.5 wt. % and particularly preferably 0.05-5 wt. % of reaction product, based on the weight of gaseous mixture.

All the compositions given in this document are based on the weight of the particular components relative to the weight of the particular total stream, unless defined otherwise in the corresponding passages.

The separation according to the invention of the gas stream leaving step a), containing HCl and the unreacted excess phosgene from the reaction, can have various embodiments. One suitable method is partial condensation followed by washing. Complete or partial condensation followed by stripping is also suitable. Another suitable embodiment of this process step is absorption in a solvent. In particular, the absorption is effected in a solvent that is also used for the quenching. It is particularly preferable to use the same solvent as that used in the quenching.

In one preferred embodiment, step b) is carried out by absorption. In one particularly preferred embodiment, the absorption takes place in a sequence of at least 2 absorption steps, optionally in combination with partial condensation stages, at least one absorption step being carried out isothermally and at least one adiabatically. Very particularly preferably, the first absorption step is carried out isothermally and the following one adiabatically. In the preferred embodiment, the absorption takes place in the solvent used for the reaction. In one particularly preferred embodiment, the same solvent as that used in the reaction is also used for both the adiabatic and isothermal absorption steps. According to another preference, the gas leaving the last absorption stage is further purified by condensing out residual traces of phosgene and solvent by cooling with a heat exchanger. In one preferred embodiment, the isothermal absorption and following adiabatic absorption are carried out in one apparatus, it also being particularly preferable to use the same apparatus to cool the gas stream leaving the absorption stage. This has the advantage of reducing the number of flanges and contributing to an increase in safety when handling phosgene. It also has the advantage of saving energy, since energy losses in the connecting pipelines are minimized by the compact design in one apparatus.

In one very particularly preferred embodiment, the gaseous mixture leaving step a) is partially condensed before entering the absorption stage, to give a liquid stream and a gas stream. Preferably, this condensation is carried out in such a way that the liquid stream contains phosgene, optionally solvents and only small amounts of dissolved HCl, and so that the gas stream contains HCl and optionally phosgene and inert gases. The gas stream obtained in the partial condensation is fed into the absorption stage. The condensation stage preferably takes place at temperatures of −40-0° C., particularly preferably at temperatures of −20-0° C. The condensation preferably takes place in a shell-and-tube heat exchanger, very preferably in a vertical shell-and-tube heat exchanger. Particularly preferably, the streams flow through the apparatus from top to bottom. Solvents can optionally be added to improve the condensing action. The solvent temperature is preferably below 10° C., particularly preferably below 0° C. The solvent may or may not contain phosgene.

In another very particularly preferred embodiment, the vapours from the condensation stage are subsequently passed in countercurrent through the solvent used in the reaction, whereby the phosgene, optionally together with traces of HCl and/or inert gases and/or reaction by-products, is absorbed in the solvent. Preferably, the gas rises through the absorption stages from bottom to top and the solvent runs through the absorption stages under gravity from top to bottom. In one particularly preferred embodiment, the liquid stream obtained in the condensation stage is combined at the bottom of the apparatus with the liquid streams flowing out of the absorption stages.

In another preferred embodiment, solvent at a temperature of −40-0° C., preferably of −20 to −10° C., is used for the adiabatic absorption step. According to a further preference, this solvent contains less than 1000 ppm, preferably less than 500 ppm and particularly preferably less than 250 ppm of phosgene. In one particularly preferred embodiment, the solvent already loaded with phosgene from the adiabatic absorption step is used for the isothermal absorption. However, it is also conceivable to carry out the isothermal absorption step either additionally or exclusively with other phosgene-containing solvent streams, e.g. those obtained in the distillation stage of phosgenation plants. In one preferred embodiment, the adiabatic temperature rise is 0.1-20° C., especially 2-5° C. The amount of solvent introduced in the absorption step is 0.1-5 times, preferably 0.15-3 times, the weight of gaseous mixture entering process step a). The choice of introduced amount, temperature and composition of the solvent used, optionally in combination with adjustment of the process parameters, e.g. pressure and temperature in the HCl/phosgene separation, makes it possible to influence the quality of the gas stream exiting the absorption stage in step b) and the composition of the liquid stream containing phosgene leaving step b).

The isothermal absorption step is preferably carried out in a shell-and-tube heat exchanger, especially a vertical one. The liberated heat of absorption in the washing liquor is thereby transferred directly to the surface of the heat exchanger as it is produced, and dissipated. Preferably, the apparatus is cooled on the jacket side and the cooling medium enters at a temperature of −40 to 0° C., particularly preferably of −25 to −10° C. The number of tubes can vary within wide limits and is restricted only by the technical ability to manufacture them. It is conceivable to have apparatuses with 100 to 6000 tubes having a length of 1 to 10 m, preferably of 3 to 8 m. The tube diameter can vary between 10 and 200 mm and is preferably in the range 20-100 mm. To enlarge the contact area, the tubes can optionally be completely or partially filled with a filling material. Various appropriate packings or filling body systems are known to those skilled in the art.

The gas stream leaving the isothermal absorption step preferably contains essentially HCl and inert gases, together with residual amounts of as yet unabsorbed phosgene. The gas temperature is normally between −20° C. and 10° C., preferably between −20 and 0° C. The gas stream leaving the isothermal absorption step normally still contains up to 5 wt. %, preferably up to 4 wt. % and particularly preferably up to 3 wt. % of phosgene, based in each case of the weight of gaseous mixture. The gas stream leaving the isothermal absorption step normally still contains more than 0.05 wt. %, preferably more than 0.1 wt. % and especially more than 0.15 wt. % of phosgene, based in each case of the weight of gaseous mixture. The adiabatic absorption step that preferably follows the isothermal absorption step is preferably carried out in a column, which can be equipped with plates, packings or filling bodies. The adiabatic absorption step has preferably 1 to 50 theoretical plates, particularly preferably 2 to 40 theoretical plates. The absorption column can have a length of 2-25 meters, preferably of 3-18 meters. The diameter of the column is restricted only by the technical ability to manufacture it and is normally in the range 250-5000 mm, preferably in the range 500-4000 mm.

In one preferred embodiment, the overall pressure loss over the isothermal and adiabatic absorption stages is less than 250 mbar, preferably less than 200 mbar and particularly preferably less than 150 mbar. This means that the pressure of the gas entering the isothermal absorption stage is not more than 250 mbar higher, preferably not more than 200 mbar higher and particularly preferably not more than 150 mbar higher than the pressure of the gas exiting the adiabatic absorption stage.

The liquid streams flowing out of the absorption stage(s) and condensation stage(s) preferably now have only a very small loading of dissolved HCl and/or dissolved inert gases and can be passed without further purification on to the second process step according to the invention, namely phosgene gas production. Preferably, the streams flowing out of the condensation stage and the absorption stage are combined and passed as a common stream on to the second process step of phosgene gas production in step c).

In another preferred embodiment, step b) is carried out by absorption in a column, the heat of absorption being dissipated by means of external coolers. In this particular embodiment, the gaseous mixture leaving step a) is first partially condensed. The residual gas stream is introduced into the bottom of an absorption column and washed in countercurrent with the solvent, the heat of absorption being dissipated by means of external heat exchangers. This can preferably be done by removing all or part, preferably all, of the liquid at various points on the absorption column and cooling it by means of an external cooler, the liquid being cooled preferably by more than 5° C., especially by more than 10° C. Preferably, the liquid is then fed back into the absorption column below the respective withdrawal point. The absorption column normally has 1-50 theoretical plates, preferably 1-30 theoretical plates. It can be equipped with packings, filling bodies or plates, preferably packings and plates. The absorption in the column is preferably carried out adiabatically between the liquid withdrawal points, the adiabatic temperature rise normally being in the range 0.1-20° C., preferably 0.1-10° C.

Another possible embodiment of the implementation of step b) is partial or complete condensation of the phosgene, then distillation or stripping in a column to remove the dissolved HCl from the phosgene bottom product, and then washing of the HCl top product obtained in the first step with a solvent in order to absorb the phosgene remaining in the gas stream after condensation.

In this embodiment the gaseous mixture leaving step a) is first completely or partially condensed in one or more apparatuses, optionally at different temperature levels. The partial or complete condensation is carried out at temperatures between −40 and 0° C., preferably at −40 to −10° C. This produces a liquid stream containing phosgene and/or solvents and/or reaction by-products, together with dissolved inert gases and dissolved HCl, and a gas stream containing essentially HCl and uncondensed phosgene.

Because the liquid stream still contains excessive amounts of dissolved HCl and/or dissolved inert gases, making the apparatuses in the following process steps unnecessarily large, stripping or distillation is needed to reduce the proportion of dissolved HCl and/or dissolved inert gases. Also, because the HCl gas stream obtained in the condensation still contains excessive amounts of uncondensed phosgene, making it necessary to purify the HCl further, this stream has to be washed.

Preferably, both streams are jointly or separately passed into a distillation column. The column preferably has an enriching section or a stripping section. Preferably, the enriching section has 1-20 theoretical plates and the stripping section likewise has 1-20 theoretical plates. The distillation column can be equipped with plates, packings or filling bodies. The streams are preferably fed in between the stripping and enriching sections of the column. Preferably, the distillation to remove the content of dissolved HCl and/or dissolved inert gases is operated at a bottom temperature of 5-150° C., preferably at 5 to 50° C. The top distillation temperature is normally in the range −20 to 30° C., preferably −10-0° C.

Preferably, the differential pressure in the distillation column, i.e. the pressure difference between the lowest and highest separating elements, is smaller than 250 mbar, preferably smaller than 200 mbar.

As an alternative to distillation, the liquid stream can be stripped, e.g. with nitrogen.

The liquid stream obtained as the bottom product of distillation or stripping is now loaded with only a small amount of dissolved HCl and/or inert gases and can be passed on to step c).

Apart from HCl, the vapour stream issuing from the distillation or stripping column also contains significant amounts of phosgene, so it is reasonable to treat this stream further if as much of the phosgene as possible is to be recovered. In one possible embodiment, the vapour stream from the column, together with the gas stream obtained in the condensation stage, is washed with a solvent. Preferably, the washing is carried out with the same solvent as that used in the phosgenation reaction. This is preferably done by bringing the gas into contact with the solvent in countercurrent; particularly preferably, the gas flows from bottom to top while the solvent runs under gravity from top to bottom. The washing is normally carried out at a top temperature of −40-10° C., preferably of −15-0° C., and preferably adiabatically, the adiabatic temperature rise normally being in the range 0.1-20° C., preferably 0.1-10° C. Another possibility is to dissipate the heat of absorption by means of external coolers, e.g. by withdrawing all or part of the liquid at one or more points and recycling it after cooling. The scrubber can be equipped with packings, filling bodies or plates. It normally has 1-25 theoretical plates. A liquid stream containing essentially solvent and phosgene is obtained at the bottom of the scrubber, and a gas stream containing essentially HCl and/or traces of phosgene and/or traces of solvent is obtained at the top of the scrubber. To further improve the purity of the gas stream, it is advantageous to condense out the traces of phosgene and/or solvent by cooling the stream further in a heat exchanger.

In this embodiment the liquid stream obtained from the scrubber is preferably mixed with the liquid stream obtained from the bottom of the distillation column and passed on to step c) as a combined stream.

The alternative processes described for carrying out step b) all produce a gas stream and a liquid stream. The gas stream containing HCl is of adequate purity and can generally be processed further without additional purification.

The gas stream containing HCl leaving step b) contains essentially HCl and optionally traces of phosgene. Apart from HCl, the stream can also contain inert gases and/or solvents, together with traces of reaction by-products. The stream contains 80-100 wt. %, preferably 90-100 wt. % and particularly preferably 95-100 wt. % of HCl, based on the weight of gas stream containing HCl. This gas stream contains at most 0.8 wt. %, preferably at most 0.4 wt. % and particularly preferably at most 0.2 wt. % of phosgene, based on the weight of gas stream containing HCl. For energy optimization it may be preferable to allow at least 1 ppm by weight of phosgene, preferably at least 5 ppm by weight of phosgene, based on the weight of gas stream containing HCl, in the gas stream leaving step b). This stream can also contain 0-10 wt. %, preferably 0.01-7.5 wt. % and particularly preferably 0.05-5 wt. % of inert gases, based on the weight of gas stream containing HCl, as well as 0-1 wt. %, preferably 0.001-0.5 wt. % and particularly preferably 0.05-0.2 wt. % of solvent, based on the weight of gas stream containing HCl. The possible content of reaction by-products is normally at most 1 wt. %, preferably at most 0.5 wt. % and particularly preferably 0.25 wt. %, based on the weight of gas stream containing HCl.

The gas stream exiting process step b) is normally under a pressure of 1 to 4 bar absolute, preferably of 1.01 to 3 bar absolute and particularly preferably of 1.02 to 2 bar absolute, and normally at a temperature of −40 to 30° C., preferably of −20 to 20 and particularly preferably of −15 to 10° C. The exit from the process step is understood as meaning the gas discharge port of the last apparatus belonging to this process step.

Apart from phosgene, the liquid stream containing phosgene leaving step b) can normally also contain solvent and/or dissolved HCl and/or dissolved inert gases, optionally together with dissolved reaction by-products. This stream contains 30-90 wt. %, preferably 35-85 wt. %, particularly preferably 38-75 wt. % and very particularly preferably 40-70 wt. % of phosgene, based on the weight of liquid stream containing phosgene. This stream can also contain 10-70 wt. %, preferably 15-65 wt. % and particularly preferably 25-60 wt. % of solvent, based on the weight of liquid stream containing phosgene, as well as 0-5 wt. %, preferably 0.1-3.5 wt. % and particularly preferably at most 0.5-2.5 wt. % of dissolved HCl, based on the weight of liquid stream containing phosgene. This liquid stream can also optionally contain dissolved inert gases in a total amount of at most 1 wt. %, preferably of at most 0.5 wt. % and particularly preferably of 0.1 wt. %, based on the weight of liquid stream containing phosgene. This stream contains a total of 1 ppm by weight, preferably 10 ppm by weight, of dissolved inert gases, based on the weight of liquid stream containing phosgene. The content of any reaction by-products present is normally 0-5 wt. %, preferably 0.001-3 wt. % and particularly preferably 0.05-2.5 wt. %, based on the weight of liquid stream containing phosgene.

The liquid stream containing phosgene exiting the first process step is normally at a temperature of −40 to 20° C., preferably of −25 to 15° C., particularly preferably of −20 to 10° C. and very particularly preferably of −15 to 8° C. On exiting the process step, said stream is normally under a pressure of 1 to 4 bar absolute, preferably of 1.01 to 3 bar absolute and particularly preferably of 1.02 to 2 bar absolute. Exit from the process step for the liquid stream containing phosgene is understood as meaning the liquid discharge port of the apparatus(es) belonging to this process stage, the pressure measured at this point being corrected for the hydrostatic pressure of the liquid column in the apparatus(es).

The low content according to the invention of dissolved HCl and/or dissolved inert gas in the liquid stream containing phosgene produced in step b) has an advantageous effect in energy terms on the phosgene gas production in step c) because the total amount of gas to be produced in step c) is smaller as a result, so it requires a lower energy expenditure in step c). Moreover, the low content according to the invention of dissolved HCl and/or dissolved inert gas in the liquid stream containing phosgene produced in step b) does not create an intolerable inert gas burden in the downstream apparatuses along the phosgene gas path.

Phosgene Gas Production (Step c))

According to the invention, the liquid stream containing phosgene obtained from the HCl/phosgene separation in step b) is passed on to the phosgene gas production in step c). Because, according to the invention, the gas leaving the phosgene gas production in step c) is under a higher pressure than the liquid stream containing phosgene leaving the HCl/phosgene separation in step b), the liquid stream passed from step b) to step c) must overcome a pressure difference. This can be done through gravity by skillfully placing the apparatuses at different heights, or by applying a gas pressure. It is preferably done by means of a pump. The liquid stream can be transferred from step b) to step c) continuously or batchwise, preferably continuously.

According to the invention, the phosgene gas production in step c) is carried out in such a way that the liquid stream containing phosgene obtained from step b) is separated in step c) into a gas stream and a liquid stream. This can preferably be effected by distillation or partial evaporation.

In one preferred embodiment, the phosgene gas production in step c) is carried out in such a way that the liquid stream containing phosgene from step b) is separated into a gas stream containing essentially phosgene and inert gases, and a liquid stream. According to the invention, the pressure in this process step (step c)) is higher than the pressure of the liquid stream obtained in the HCl/phosgene separation (step b)).

In one preferred embodiment, the phosgene gas production in step c) takes place in a distillation column with 1-80 theoretical plates, preferably 2-45 theoretical plates. The column can contain a stripping section and/or an enriching section, preferably both. Preferably, the stripping section has 1-40 theoretical plates, particularly preferably 1-20 theoretical plates, and the enriching section has 1-40 theoretical plates, particularly preferably 1-20 theoretical plates. The distillation column can be equipped with plates, packings or filling bodies, plates or packings being preferred. Suitable plates or packings are known to those skilled in the art, examples which may be mentioned, without implying a limitation, being sheet metal or woven fabric packings with structure, or bubble-cap, sieve or valve plates.

The column is normally operated at a bottom temperature of 100 to 250° C., preferably of 120 to 230° C. and particularly preferably of 140-220° C.

The differential pressure in the distillation column is normally smaller than 400 mbar, preferably smaller than 300 mbar and especially smaller than 200 mbar. Differential pressure is to be understood here as meaning the pressure difference between the top and bottom of the column.

In one preferred embodiment, the column is provided with a top condenser, which is particularly preferably inserted in the column. The top condenser is normally operated at a cooling medium entry temperature of −40 to 20° C., preferably at −30 to 10° C. and particularly preferably at −25 to 0° C. In one particularly preferred embodiment, the differential pressure of the gas across the top condenser is smaller than 150 mbar, particularly preferably smaller than 100 mbar. All or part of the condensate produced by the top condenser can be recycled into the column and/or withdrawn; preferably, all of the condensate is recycled into the column.

The energy supply at the bottom of the column can be provided by any conceivable evaporator, examples being natural-circulation evaporators, rising-film evaporators and falling-film evaporators. Falling-film evaporators are particularly preferred.

In one preferred embodiment, the liquid stream obtained from step b) is fed into the middle of the column, preferably between the enriching and stripping sections of the column.

In one particularly preferred embodiment, the column additionally has a top feed, said feed preferably being positioned above the enriching section. In one particularly preferred form, this is a liquid feed position. In one very particularly preferred embodiment, liquid phosgene is introduced through this feed position.

The liquid phosgene optionally fed into the top of the column is normally at a temperature of −30 to 10° C., preferably of −20 to 0° C. This stream normally contains essentially phosgene, i.e. the phosgene content is between 95 and 100 wt. %; preferably, the phosgene content is between 98 and 100 wt. %, based on the weight of this stream. The energy requirement can be reduced by feeding liquid phosgene into the top of the column.

In another embodiment, the column can additionally have a feed position for a gas stream. This feed position is preferably located below or above the enriching section or else below the stripping section.

In another possible embodiment, the phosgene gas production in step c) is carried out in such a way that the liquid stream containing phosgene from step b) is separated by partial evaporation into a gas stream containing phosgene and optionally inert gases, and a liquid stream. Here, according to the invention, the pressure in the phosgene gas production in step c) is higher than the pressure of the liquid stream obtained in the HCl/phosgene separation (step b)).

For this purpose the liquid stream obtained from step b) is fed into an evaporator, which is heated by an external heating medium. The bottom temperature of the evaporator is in the range from 30 to 250° C., preferably from 70 to 230° C. and particularly preferably in the range 100-220° C.

In addition to the liquid stream from step b), another liquid phosgene stream can also be introduced into the evaporator. This other liquid phosgene stream is normally at a temperature of −30 to 10° C., preferably of −20 to 0° C. The stream normally contains essentially phosgene, i.e. the phosgene content is between 95 and 100 wt. %; preferably, the phosgene content is between 98 and 100 wt. %, based on the weight of this stream.

The liquid is partially evaporated in the evaporator, i.e. there is a discontinuous or, preferably, continuous discharge of liquid from the evaporator.

It is further possible to support the phosgene gas production in the various embodiments, e.g. by blowing in inert gases such as nitrogen.

The gas stream obtained in the phosgene gas production in step c) contains essentially phosgene. Apart from phosgene, this stream can also contain inert gases and/or solvents and/or reaction by-products and/or HCl. It normally contains 80-100 wt. %, preferably 85-99.9 wt. %, particularly preferably 90-99.8 wt. % and very particularly preferably 92-99.7 wt. % of phosgene, based on the weight of the gas stream. This stream can also contain up to 20 wt. % of vaporous solvent, preferably up to 15 wt. % and particularly preferably between 5 wt. % and up to 10 wt. % of solvent, based on the weight of the gas stream. To optimize the energy input, it is reasonable to allow this gas stream to have a certain solvent content, which is normally at least 5 ppm by weight, preferably at least 10 ppm by weight and particularly preferably at least 25 ppm by weight, based on the weight of the gas stream. This stream can normally contain a total of at most 1 wt. %, preferably at most 0.5 wt. % and particularly preferably 0.1 wt. % of inert gases, based on the weight of the gas stream. It can also contain at most 5 wt. %, preferably at most 4.0 wt. % and particularly preferably at most 3.5 wt. % of HCl, based on the weight of the gas stream. The content of any reaction by-products present is normally up to 5 wt. %, preferably up to 4 wt. % and particularly preferably up to 2.5 wt. %, based on the weight of the gas stream. The gas stream containing phosgene obtained in the phosgene gas production is normally at a temperature of −10-100° C., preferably of 0-80° C. and particularly preferably of 5-70° C. on exiting this process step. The pressure of the gas stream obtained is normally 1.05 to 6 bar absolute, preferably 1.3 to 6 bar and particularly preferably 1.6 to 6 bar on exiting this process step. Exit from the process stage is understood as meaning the gas discharge port of the apparatus(es) in which step c) is carried out.

According to the invention, the pressure of the gas stream containing phosgene obtained in step c) is always higher than the pressure of the liquid stream containing phosgene obtained in step b), the required pressure difference relating to the pressure of the gas stream containing phosgene on exiting the apparatus(es) in which step c) is carried out, and the pressure of the liquid stream containing phosgene obtained in step b) on exiting the apparatus(es) in which step b) is carried out, corrected for the hydrostatic pressure of the liquid column in the apparatus(es). Normally this pressure difference is preferably at least 50 mbar, particularly preferably at least 100 mbar and very particularly preferably at least 250 mbar; it generally does not exceed 100 bar. The pressure difference can preferably be applied by means of a pump for the liquid stream containing phosgene obtained in step b), said pump preferably being located between the apparatuses in which steps b) and c) are carried out.

Moreover, the pressure of the gas stream containing phosgene obtained in step c) is preferably always higher than the pressure of the gas stream containing HCl obtained in step b), the pressure difference between the exit of the gas stream from step c) and the exit of the gas stream containing HCl from step b) being preferably at least 50 mbar, preferably at least 100 mbar and particularly preferably at least 250 mbar. The pressure difference between step b) and step c) generally does not exceed 100 bar.

Therefore, in step d), as a result of this pressurization, the gas stream containing phosgene leaving the phosgene gas production in step c) can preferably be passed on to the reaction in step a) without using a pressure-raising element in the gas path. Dispensing with a pressure-raising element in the gas path improves the safety of the process because it is no longer necessary to provide rotating parts with gastight seals, which is difficult in terms of safety regulations. Likewise, all or part of the gas stream formed in the reaction in step a) can then preferably be passed on to the HCl/phosgene separation in step b) without using pressure-raising elements. Particularly preferably, the use of pressure-raising elements for the phosgene circuit (steps a) to d)) is thus completely dispensed with on the gas side.

The liquid stream obtained in the phosgene gas production in step c) consists essentially of solvent. In addition to the latter, this stream can also contain reaction by-products. It can further contain certain amounts of phosgene. This liquid stream normally contains 80-100 wt. %, preferably 85-99.9 wt. %, particularly preferably 90-99.8 wt. % and very particularly preferably 95-99.7 wt. % of solvent, based on the weight of the liquid stream.

This stream can also contain up to 20 wt. %, preferably up to 15 wt. %, particularly preferably up to 10 wt. % and very particularly preferably up to 7 wt. % of dissolved phosgene, based on the weight of the liquid stream. To optimize the energy input, it is reasonable to allow this liquid stream to have a certain phosgene content, which is normally at least 1 ppm by weight, preferably at least 3 ppm by weight and particularly preferably at least 8 ppm by weight, based on the weight of the liquid stream. This stream is normally loaded with a total of at most 0.5 wt. %, preferably at most 0.1 wt. % and particularly preferably 0.05 wt. % of dissolved inert gases, based on the weight of the liquid stream. It can also contain at most 1 wt. %, preferably at most 0.1 wt. % and particularly preferably at most 0.05 wt. % of HCl, based on the weight of the liquid stream. The content of any reaction by-products present is normally up to 5 wt. %, preferably up to 4 wt. % and particularly preferably up to 2.5 wt. %, based on the weight of the liquid stream.

To optimize the energy consumption of the process steps according to the invention, it is optionally reasonable for the liquid stream containing phosgene obtained in the HCl/phosgene separation in step b) to be passed on to the phosgene gas production in step c) directly, i.e. without further changes in process technology, or indirectly, i.e. after further changes in process technology.

Changes in process technology are understood in terms of this patent as meaning changes in composition, pressure or temperature.

Preferably, the liquid stream obtained from step b) is passed indirectly on to the phosgene gas production in step c). Particularly preferably, the temperature of the liquid stream is changed, preferably raised, the increase in temperature of the stream between the exit from step b) and the entry into step c) normally being between 0.5 and 220° C., preferably between 1 and 200° C. and particularly preferably between 5 and 175° C.

Particularly preferably, the temperature is raised by exchange with at least one other liquid material stream in the plant. This exchange preferably takes place in a heat exchanger such as a shell-and-tube heat exchanger or a plate-type heat exchanger, preferably a shell-and-tube heat exchanger.

To minimize the expenditure on apparatuses and hence the investment costs, it is reasonable to restrict the total number of apparatuses in which these changes in process technology are applied to the stream. In general, these changes in process technology are applied in no more than 15 apparatuses in series, preferably in no more than 10 apparatuses in series and particularly preferably in no more than 8 apparatuses in series. This restriction reduces the number of connecting pipelines and flanges and hence the risk of leakage, thus increasing the safety of the process.

To optimize the energy consumption of the process steps according to the invention, it is optionally reasonable to apply changes in process technology to the liquid stream obtained in step c) before using it further in the overall process.

All or part of this stream can optionally be used as solvent in the Ha/phosgene separation in step b). This is particularly advantageous for removing low-boiling reaction products, together with the gas stream obtained in step b), from the process.

The process according to the invention makes it possible to achieve a high phosgene recovery yield. Phosgene recovery yield is understood as meaning the proportion of phosgene which, via step b) according to the invention, is separated from the gaseous mixture leaving the reactor, containing at least HCl and the unreacted excess phosgene from the reaction, and which, via the gas stream obtained in step c), is recycled into the reaction according to step a).

The phosgene recovery yield is calculated by forming the quotient in percent of the amount of phosgene in the gas stream entering process step b) and the amount of phosgene in the gas stream exiting process step c), and subtracting any fresh phosgene that has been fed in.

In general, the phosgene recovery yield is more than 90%, especially more than 93%, preferably more than 95% and particularly preferably more than 98%.

The process according to the invention offers the advantageous possibility to dispense with the use of pressure-raising elements for gaseous phosgene in the whole of the phosgene gas space. The preferred omission of these units increases the safety of the production plant because they often have shaft seals, which are expensive in terms of technology and problematical in terms of safety regulations when gaseous phosgene is used. Furthermore, the use of pressure-raising elements is often energy-intensive, so the energy requirement of the plant is improved by omitting them.

Pressure-raising elements are to be understood in terms of the present patent as meaning an industrial unit which raises the pressure of a gas stream. This means that the pressure of the gas entering the unit is lower than the pressure of the gas exiting the unit. Examples of conceivable pressure-raising elements are compressors, condensers or jets.

In terms of the present invention, phosgene gas space is to be understood as meaning the gas space in which a significant amount of phosgene is present in gaseous form. Significant amount of phosgene is to be understood as meaning that the phosgene content of the gas space is >1 wt %. In particular, whole of the phosgene gas space is to be understood as meaning the region starting with the process section of phosgene gas production (step c)), phosgene recycling (step d)), phosgenation (step a)) and HCl/phosgene separation (step b)), as well as phosgene production.

Phosgene Recycling (Step d))

All or part of the gas stream obtained from step c) in the process according to the invention is recycled into the reaction according to step a). Preferably, all of this stream is recycled into the reaction according to step a). In particular, it is not necessary to recycle part of the gas stream obtained in step c) into the HCl/phosgene separation (step b)).

It is conceivable for the gas stream obtained in step c) to be distributed among the reactors with or without regulation; a regulated distribution is preferred. The number of reactors into which the gas stream obtained from step c), optionally in combination with a gas stream obtained in phosgene production, is introduced must be at least one. However, a larger number of reactors is also conceivable, said number preferably being below 20. It is also conceivable that in the case where more than one reactor is used, one or more reactors receive exclusively fresh phosgene, while the remaining reactors are supplied exclusively with the gas stream obtained from the phosgene gas production in step c).

A further possibility is for the gas streams obtained from several reactors in step a) to be combined before being passed on to the HCl/phosgene separation in step b). Preferably, up to 20 reactors with their respective gas streams leaving step a) are associated with a common HCl/phosgene separation in step b). For this purpose the gas streams can be passed on to process step b) together, separately or partially combined. The isocyanates prepared in process step a) can be identical or different.

The fresh phosgene required for the phosgenation, i.e. the phosgene normally produced by reacting chlorine with carbon monoxide, can be introduced into the process according to the invention in different ways. In terms of the present patent application, fresh phosgene is understood as meaning phosgene which does not originate directly from the process according to the invention. It is preferably phosgene which, after the phosgene synthesis, usually from chlorine and carbon monoxide, does not pass through a reaction stage with a phosgene conversion of more than 5% of the conversion of the phosgene prepared in the phosgene synthesis.

On the one hand it is possible to use the fresh phosgene in gaseous form. This gaseous phosgene can be mixed with the gas stream obtained from the phosgene gas production in step c) and passed as a common stream to the phosgenation reactors in step a). This is known in the state of the art, e.g. from EP-A-2 028 179. The gaseous fresh phosgene, optionally in combination with a gaseous stream obtained in the phosgene production in step c), can be passed, together or separately, to the reactors for the phosgenation reaction in step a).

It is also possible to pass the gaseous fresh phosgene stream obtained in the phosgene production, together with the stream leaving the reactor, on to the HCl/phosgene separation in step b). According to the teaching of EP-A-1849 767, this is advantageous for stripping impurities out of the HCl to give a particularly pure HCl stream.

A further possibility is to pass the fresh phosgene in gaseous form on to the phosgene gas production in step c). This is advantageous because the introduction of gas facilitates the evaporation of the liquid stream in this process step due to the stripping effect.

If the fresh phosgene is introduced in gaseous form into the process according to the invention, the pressure in the phosgene production is higher than the pressure of the gas stream obtained in step c). Normally the pressure in the phosgene production is at least 50 mbar higher, preferably at least 80 mbar higher and particularly preferably at least 100 mbar higher than the pressure in step c). The pressure difference between the phosgene production and the gas stream obtained in step c) is normally not more than 100 bar.

On the other hand it is possible first to liquefy the fresh phosgene, thereby purifying it by removing as much as possible of the inert gases and by-products of the phosgene preparation. In this case the resulting liquid phosgene can be passed on to the HCl/phosgene separation in step b). However, it is also possible to pass this liquid phosgene on to the phosgene gas production in step c). A further possibility is for the liquid phosgene produced in this way to be evaporated in a separate apparatus to give a gaseous phosgene stream, which can be introduced into the process according to the invention in accordance with the possibilities described in the previous paragraph.

If the fresh phosgene is first liquefied, the pressure in the phosgene production is independent of the pressure in step c), i.e. the pressure in the phosgene production can be higher than, equal to or lower than the pressure in step c); normally the pressure in the phosgene production (fresh phosgene) is higher than the pressure in step c). The only essential feature is that the liquefied fresh phosgene is fed into the process according to the invention. This can be done through gravity by skillfully placing the apparatuses at different heights, or by applying a gas pressure. It is preferably done by means of a pump. The liquefied fresh phosgene can be transferred to the process according to the invention continuously or batchwise, preferably continuously.

Preferably, by associating the phosgene production with the process according to the invention in the manner described, the fresh phosgene can be fed into the process according to the invention without using a pressure-raising element in the gas path. Dispensing with a pressure-raising element in the gas path improves the safety of the process because it is no longer necessary to provide rotating parts with gastight seals, which is difficult in terms of safety regulations.

According to the invention, the pressure of the gas stream containing phosgene obtained in step c) is always higher than the pressure of the liquid stream containing phosgene obtained in step b). Moreover, the pressure of the gas obtained in step c) is preferably always higher than the pressure of the gas obtained in step b). Furthermore, the pressure in step a) is lower than the pressure of the gas obtained in step c). Also, the pressure in step a) is higher than the pressure of the gas obtained in step b). It thus follows that, for the overall process consisting of step a) (gas-phase phosgenation), step b) (HCl/phosgene separation) and step c) (phosgene gas production), the pressure is highest in step c) and lowest in step b), while the pressure in step a) is between the pressures in steps c) and b). This process according to the invention makes it possible to dispense with the use of pressure-raising elements for gaseous phosgene in the whole of the phosgene gas space and hence to improve the safety of the plant.

The pressure difference that is normally present between the exit of the gas stream from step c) and the exit of the gas stream containing HCl from step b), being at least 50 mbar, preferably at least 100 mbar and particularly preferably at least 250 mbar, ensures that the gas flows without an additional pressure-raising element from the phosgene gas production (step c)) via the gas phase phosgenation (step a)) to the HCl/phosgene separation (step b)). It is not an essential feature of the invention how the overall pressure difference between step c) and step b) is divided, provided that the pressure difference between step c) and step a) is at least 20 mbar and the pressure difference between step a) and step b) is at least 20 mbar. This pressure difference ensures that the gas flow is sufficiently rapid to be able to dispense with the use of a pressure-raising element in the phosgene gas space.

EXAMPLES

Within the framework of this patent application, data in ppm are to be understood as being by weight (ppm by weight). Data in mbara denote the absolute pressure in mbar.

Example 1 (According to the Invention)

In a tubular reactor with downstream isocyanate condensation stage, a mixture consisting of gaseous 2,4- and 2,6- toluylenediamine and nitrogen as inert gas is reacted together with a phosgene gas stream by mixing in a nozzle. The reactor pressure is 1600 mbara and the reaction temperature approx. 450° C. A liquid stream containing 2,4- and 2,6-toluylene diisocyanate and a gas stream containing phosgene and HCl are obtained. The stream containing isocyanate was purified by distillation to give pure toluylene diisocyanate.

The gas stream containing HCl and phosgene is separated by a three-stage procedure into an HCl gas stream and a liquid stream containing phosgene. First the stream is partially condensed and then the residual gas is passed through an isothermal absorption step followed by an adiabatic absorption step. Also, cold solvent at a temperature of −11° C. is fed into the top of the adiabatic absorption step and flows through the absorption steps in countercurrent with the gas. HCl gas with a phosgene content of less than 50 ppm by weight is withdrawn from the top of the absorption column and a solution consisting of ODB and phosgene is obtained at the liquid level at the bottom of the absorption column under a pressure of approx. 1400 mbara. The pressure of the HCl gas at the top of the absorption column is 1300 mbara.

The resulting phosgene solution is pumped into the phosgene gas production, which takes the form of a desorption column. The inflow is situated between the stripping and enriching sections of the column. A gas stream containing 94.4 wt. % of phosgene and 4.4 wt. % of HCl is withdrawn from the top of the column under a pressure of 1800 mbara. This stream is mixed in gaseous form with a phosgene gas stream (fresh phosgene) from the phosgene production and conveyed to the nozzle of the tubular reactor.

No pressure-raising element is used in the whole of the phosgene gas space. The phosgene recovery yield is 98.3%.

Example 2 (According to the Invention)

In the first phosgenation line of a two-line plant for the preparation of diisocyanates by gas-phase phosgenation, in a tubular reactor with downstream isocyanate condensation stage, a mixture consisting of gaseous isophoronediamine and nitrogen as inert gas is reacted together with a phosgene gas stream, introduced directly from the phosgene production, by mixing in a nozzle. The reactor pressure is 1300 mbara and the reaction temperature approx. 400° C. The reaction mixture is cooled considerably by the removal of heat, with or without the addition of solvent, to give, at the exit from the cooling zone, a liquid phase containing essentially isophorone diisocyanate and an isocyanate-free gas phase containing essentially the excess phosgene and the HCl by-product. The stream containing isocyanate is purified by distillation to give pure isophorone diisocyanate.

In the second phosgenation line of a two-line plant for the preparation of diisocyanates by gas-phase phosgenation, in a tubular reactor with downstream isocyanate condensation stage, a mixture consisting of gaseous 1,6-diaminohexane and nitrogen as inert gas is reacted together with a phosgene gas stream consisting of a mixture of a phosgene gas stream (fresh phosgene) from the phosgene production and a phosgene gas stream from a desorption column, by mixing in a nozzle. The reactor pressure is 1300 mbara and the reaction temperature approx. 430° C. The reaction mixture is cooled considerably by the removal of heat, with or without the addition of solvent, to give, at the exit from the cooling zone, a liquid phase containing essentially 1,6-hexane diisocyanate and an isocyanate-free gas phase containing essentially the excess phosgene and the HCl by-product. The stream containing isocyanate is purified by distillation to give pure 1,6-diisocyanatohexane.

The gas streams containing HCl and phosgene from both the phosgenation lines are combined and jointly separated by a three-stage procedure into an HCl gas stream and a liquid stream containing phosgene. First the stream is partially condensed and then the residual gas is passed though an isothermal absorption step followed by an adiabatic absorption step. Also, cold solvent at a temperature of −11° C. is fed into the top of the adiabatic absorption step and flows through the absorption steps in countercurrent with the gas. HCl gas with a phosgene content of less than 0.5 wt. % is withdrawn from the top of the absorption column and a solution consisting of monochlorobenzene (MCB) and phosgene is obtained at the liquid level at the bottom of the absorption column under a pressure of approx. 1150 mbara. The pressure of the HCl gas at the top of the absorption column is 1080 mbara.

The resulting phosgene solution is pumped into the phosgene gas production, which takes the form of a desorption column. The inflow is situated between the stripping and enriching sections of the column. A gas stream containing 94.4 wt. % of phosgene and 4.4 wt. % of HCl is withdrawn from the top of the column under a pressure of 1400 mbara. This stream is mixed in gaseous form with a phosgene gas stream (fresh phosgene) from the phosgene production and conveyed to the nozzle of the tubular reactor of the second phosgenation line.

No pressure-raising element is used in the whole of the phosgene gas space. The phosgene recovery yield is 98.5%.

Example 3 (According to the Invention)

In a tubular reactor corresponding to Example 1, a liquid stream containing 2,4- and 2,6-toluylene diisocyanate and a gas stream containing phosgene and HCl are obtained. The gaseous mixture containing HCl and phosgene is separated as described in Example 1. The pressure of the HCl gas leaving the absorption column at the gas discharge port is 1300 mbara and the pressure of the phosgene solution at the bottom of the apparatus, measured at the liquid discharge port, minus the pressure due to the hydrostatic liquid column, is 1400 mbara.

The resulting phosgene solution is pumped into the phosgene gas production, which takes the form of a desorption column. The inflow is situated between the stripping and enriching sections of the column. Liquid fresh phosgene is also fed in above the enriching section of the column. A gas stream containing 97.6 wt. % of phosgene and 2.4 wt. % of HCl is withdrawn from the top of the column under a pressure of 1900 mbara and recycled into the reaction.

No pressure-raising element is used in the whole of the phosgene gas space. The phosgene recovery yield is 99%.

Example 4 (According to the Invention)

In a tubular reactor corresponding to Example 1, a liquid stream containing 2,4- and 2,6-toluylene diisocyanate and a gas stream containing phosgene and HCl are obtained. The gaseous mixture containing HCl and phosgene is separated as described in Example 1. The pressure of the HCl gas leaving the absorption column at the gas discharge port is 1300 mbara and the pressure of the phosgene solution at the bottom of the apparatus, measured at the liquid discharge port, minus the pressure due to the hydrostatic liquid column, is 1400 mbara.

The resulting phosgene solution is introduced into a desorption column, which is equipped with only one enriching section having 20 theoretical plates. The feed to the column is situated below the enriching section. Phosgene gas is withdrawn from the top of the column under a pressure of 2000 mbara and recycled into the reaction. ODB containing 6.7 wt.

% of phosgene is withdrawn from the bottom of the column at a temperature of approx. 115° C.

No pressure-raising element is used in the whole of the phosgene gas space. The phosgene recovery yield is 95.6%.

Example 5 (According to the Invention)

In a tubular reactor corresponding to Example 1, a liquid stream containing 2,4- and 2,6-toluylene diisocyanate and a gas stream containing phosgene and HCl are obtained. The gaseous mixture containing HCl and phosgene is separated as described in Example 1. The pressure of the HCl gas leaving the absorption column at the gas discharge port is 1300 mbara and the pressure of the phosgene solution at the bottom of the apparatus, measured at the liquid discharge port, minus the pressure due to the hydrostatic liquid column, is 1400 mbara.

The resulting phosgene solution is pumped at a temperature below 10° C. into the top of a stripping column having 20 theoretical plates. Phosgene gas containing approx. 0.2 wt. % of solvent is withdrawn from the top of the stripping column under a pressure of 2000 mbara. Solvent containing approx. 100 ppm by weight of phosgene is withdrawn from the bottom of the stripping column.

No pressure-raising element is used in the whole of the phosgene gas space. The phosgene recovery yield is 99%.

Example 6 (According to the Invention)

In a tubular reactor with downstream isocyanate condensation stage, a mixture consisting of gaseous 1,6-diaminohexane and nitrogen as inert gas is reacted together with a phosgene gas stream, introduced directly from the phosgene production, by mixing in a nozzle. The reactor pressure is 1450 mbara and the reaction temperature approx. 450° C. The reaction mixture is cooled considerably by the removal of heat, with or without the addition of solvent, to give, at the exit from the cooling zone, a liquid phase containing essentially 1,6-diisocyanatohexane and an isocyanate-free gas phase containing essentially the excess phosgene and the HCl by-product. The stream containing isocyanate is purified by distillation to give pure 1,6-diisocyanatohexane.

The gas stream containing HCl and phosgene is separated by a three-stage procedure into an HCl gas stream and a liquid stream containing phosgene. First the stream is partially condensed and then the residual gas is passed through an isothermal absorption step followed by an adiabatic absorption step. Also, cold solvent at a temperature of −11° C. is fed into the top of the adiabatic absorption step and flows through the absorption steps in countercurrent with the gas. HCl gas with a phosgene content of less than 0.5 wt. % is withdrawn from the top of the absorption column and a solution consisting of monochlorobenzene (MCB) and phosgene is obtained at the liquid level at the bottom of the absorption column under a pressure of approx. 1250 mbara. The pressure of the HCl gas at the top of the absorption column is 1200 mbara.

The resulting phosgene solution is pumped into the phosgene gas production, which takes the form of a desorption column. The inflow is situated between the stripping and enriching sections of the column. A gas stream containing 93.3 wt. % of phosgene and 6.7 wt. % of HCl is withdrawn from the top of the column under a pressure of 1800 mbara. This stream is mixed in gaseous form with a phosgene gas stream (fresh phosgene) from the phosgene production and conveyed to the nozzle of the tubular reactor.

No pressure-raising element is used in the whole of the phosgene gas space. The phosgene recovery yield is 98.5%.

The invention claimed is:

1. A process for the production of an isocyanate comprising:
   a) reacting an amine with a stoichiometric excess of phosgene in a gas phase in a reactor at a temperature above the amine's boiling point to obtain a liquid stream containing the isocyanate and a gas stream containing hydrogen chloride and phosgene,
   b) separating the gas stream containing hydrogen chloride and phosgene produced in step a) into a gas stream containing hydrogen chloride and a liquid stream containing phosgene,
   c) converting at least part of the liquid stream containing phosgene produced in step b) to a gas stream containing phosgene,
   d) recycling the gas stream containing phosgene produced in step c) into step a), and
   e) maintaining the gas stream containing phosgene from step d) at a pressure higher than that of the liquid stream containing phosgene produced in step b).

2. The process of claim 1 in which step d) is carried out without using pressure-raising elements.

3. The process of claim 1 in which temperature of the liquid stream containing phosgene produced in step b) is raised from 0.5 to 220° C. before step c).

4. The process of claim 1 in which the gas stream containing phosgene produced in step c) contains from 80 to 100% by weight of phosgene, based on total weight of the gas stream.

5. The process of claim 1 in which the liquid stream containing phosgene produced in step b) contains from 30 to 90% by weight of phosgene, based on total weight of the liquid stream.

6. The process of claim 1 in which the pressure difference in step e) is at least 50 mbar.

7. The process of claim 1 in which the gas stream containing hydrogen chloride and phosgene obtained in step a) is not contacted with any pressure-raising element prior to separation in step b).

8. The process of claim 1 in which the liquid stream containing phosgene from step b) is pumped into step c).

* * * * *